US012127961B2

(12) United States Patent
McDonald et al.

(10) Patent No.: US 12,127,961 B2
(45) Date of Patent: Oct. 29, 2024

(54) STENT DEVICE

(71) Applicant: VASCUTEK LIMITED, Renfrewshire (GB)

(72) Inventors: Gary McDonald, Strathclyde (GB); Vincent Nelis, Renfrewshire (GB)

(73) Assignee: Vascutek Limited, Renfrewshire (GB)

(*) Notice: Subject to any disclaimer, the term of this patent is extended or adjusted under 35 U.S.C. 154(b) by 231 days.

(21) Appl. No.: 17/311,897

(22) PCT Filed: Nov. 15, 2019

(86) PCT No.: PCT/GB2019/053239
§ 371 (c)(1),
(2) Date: Jun. 8, 2021

(87) PCT Pub. No.: WO2020/128418
PCT Pub. Date: Jun. 25, 2020

(65) Prior Publication Data
US 2022/0023080 A1  Jan. 27, 2022

(30) Foreign Application Priority Data
Dec. 20, 2018  (GB) .................................... 1820898

(51) Int. Cl.
*A61F 2/07*  (2013.01)
*A61F 2/89*  (2013.01)
(Continued)

(52) U.S. Cl.
CPC .................. *A61F 2/97* (2013.01); *A61F 2/89* (2013.01); *A61F 2/966* (2013.01); *A61F 2/07* (2013.01);
(Continued)

(58) Field of Classification Search
CPC .... A61F 2/97; A61F 2/89; A61F 2/966; A61F 2/962; A61F 2002/9511; A61F 2002/075;
(Continued)

(56) References Cited

U.S. PATENT DOCUMENTS 4,580,568 A   4/1986  Gianturco
5,290,305 A   3/1994  Inoue
(Continued)

FOREIGN PATENT DOCUMENTS

AU   2010/254599 B1   2/2011
CA        2872125 A1 *  4/2011  ............... A61F 2/06
(Continued)

OTHER PUBLICATIONS

Nigro et al., "Use of the Gore Hybrid Vascular Graft in a challenging high-lying extracranial carotid artery aneurysm," J Vasc Surg, 59: 817-820 (2014).
(Continued)

*Primary Examiner* — Phong Son H Dang
*Assistant Examiner* — Lindsey R. Rivers
(74) *Attorney, Agent, or Firm* — Stephen J. Kenny; Foley Hoag LLP

(57) ABSTRACT

The present invention relates to a stent device comprising a sleeve formed with a plurality of compactable spring ring elements arranged along its length, the sleeve having compacted and expanded states. Each said ring element has an undulating profile at the surface of the sleeve so that adjacent ring elements at least partially overlap along the longitudinal extent of the device, the ring elements being compactable against their natural resilience to reduce the outer diameter of the sleeve for allowing housing of the compacted stent
(Continued)

device in a frangible sheath, with adjacent ring elements being inter-coupled so as to substantially maintain their axial spacing between the compacted and expanded states.

17 Claims, 2 Drawing Sheets

(51) Int. Cl.
  *A61F 2/95* (2013.01)
  *A61F 2/966* (2013.01)
  *A61F 2/97* (2013.01)
(52) U.S. Cl.
  CPC ............... *A61F 2002/9511* (2013.01); *A61F 2220/0075* (2013.01); *A61F 2230/0095* (2013.01); *A61F 2250/0039* (2013.01)
(58) Field of Classification Search
  CPC ........ A61F 2002/072; A61F 2220/0075; A61F 2230/0095; A61F 2250/0039
  See application file for complete search history.

(56) References Cited

U.S. PATENT DOCUMENTS

| | | | |
|---|---|---|---|
| 5,578,072 | A | 11/1996 | Barone et al. |
| 5,591,228 | A | 1/1997 | Edoga |
| 5,824,041 | A | 10/1998 | Lenker et al. |
| 5,925,074 | A | 7/1999 | Gingras et al. |
| 6,036,723 | A | 3/2000 | Anidjar et al. |
| 6,203,568 | B1 | 3/2001 | Lombardi et al. |
| 6,635,080 | B1 * | 10/2003 | Lauterjung ............... A61F 2/07 623/1.13 |
| 6,673,103 | B1 | 1/2004 | Golds et al. |
| 6,773,457 | B2 | 8/2004 | Ivancev et al. |
| 6,938,646 | B2 | 9/2005 | Litton |
| 7,780,622 | B2 | 8/2010 | Fitzpatrick et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,652,198 | B2 | 2/2014 | Andreas et al. |
| 8,740,971 | B2 | 6/2014 | Iannelli |
| 8,968,389 | B2 | 3/2015 | Greenberg et al. |
| 9,056,002 | B2 | 6/2015 | Tabor |
| 9,398,964 | B2 | 7/2016 | McGee et al. |
| 9,510,936 | B2 | 12/2016 | McDonald et al. |
| 9,622,894 | B2 | 4/2017 | McGee |
| 9,788,983 | B2 | 10/2017 | Johnson et al. |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 10,413,396 | B2 | 9/2019 | Ashton |
| 10,724,805 | B2 | 7/2020 | Barmeier et al. |
| 10,987,207 | B2 | 4/2021 | Wilger et al. |
| 11,026,823 | B2 | 6/2021 | McDonald et al. |
| 11,419,712 | B2 | 8/2022 | McDonald |
| 11,458,008 | B2 | 10/2022 | Debus et al. |
| 11,471,261 | B2 | 10/2022 | McDonald |
| 11,554,033 | B2 | 1/2023 | Kolbel et al. |
| 2003/0024527 | A1 | 2/2003 | Ginn |
| 2003/0120263 | A1 | 6/2003 | Ouriel et al. |
| 2003/0130720 | A1 | 7/2003 | DePalma et al. |
| 2003/0135257 | A1 | 7/2003 | Taheri |
| 2003/0176911 | A1 | 9/2003 | Iancea et al. |
| 2004/0117003 | A1 | 6/2004 | Ouriel et al. |
| 2004/0167618 | A1 | 8/2004 | Shaolian et al. |
| 2004/0215315 | A1 | 10/2004 | Jones et al. |
| 2004/0243221 | A1 | 12/2004 | Fawzi et al. |
| 2005/0010277 | A1 | 1/2005 | Chuter |
| 2005/0033399 | A1 | 2/2005 | Richter |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2006/0184226 | A1 | 8/2006 | Austin |
| 2006/0229700 | A1 | 10/2006 | Acosta et al. |
| 2007/0010873 | A1 | 1/2007 | Neri |
| 2007/0055347 | A1 | 3/2007 | Arbefeuille |
| 2007/0106368 | A1 | 5/2007 | Vonderwalde |
| 2007/0112422 | A1 | 5/2007 | Dehdashtian |
| 2007/0135904 | A1 | 6/2007 | Eidenschink et al. |
| 2007/0168013 | A1 | 7/2007 | Douglas |
| 2007/0208409 | A1 | 9/2007 | Quigley |
| 2008/0082159 | A1 | 4/2008 | Tseng et al. |
| 2008/0147171 | A1 | 6/2008 | Ashton et al. |
| 2008/0188924 | A1 | 8/2008 | Prabhu |
| 2009/0043330 | A1 * | 2/2009 | To ............... A61F 2/07 606/198 |
| 2009/0264991 | A1 | 10/2009 | Paul, Jr. et al. |
| 2010/0152835 | A1 | 6/2010 | Orr |
| 2010/0222869 | A1 | 9/2010 | Delaney |
| 2010/0234937 | A1 | 9/2010 | Wang et al. |
| 2011/0054586 | A1 | 3/2011 | Mayberry et al. |
| 2011/0066221 | A1 | 3/2011 | White et al. |
| 2011/0190862 | A1 | 8/2011 | Bashiri et al. |
| 2011/0230956 | A1 | 9/2011 | White |
| 2012/0059448 | A1 | 3/2012 | Parker et al. |
| 2012/0071960 | A1 | 3/2012 | Tani |
| 2012/0136431 | A1 | 5/2012 | Chen |
| 2012/0158121 | A1 | 6/2012 | Ivancev et al. |
| 2012/0172887 | A1 | 7/2012 | Hatfield |
| 2012/0239136 | A1 | 9/2012 | Bruzzi |
| 2012/0271401 | A1 | 10/2012 | Bruszewski et al. |
| 2012/0277849 | A1 | 11/2012 | Tani et al. |
| 2012/0290068 | A1 | 11/2012 | Roeder et al. |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289700 | A1 * | 10/2013 | Acosta-Acevedo ...... A61F 2/07 623/1.13 |
| 2013/0289713 | A1 | 10/2013 | Pearson et al. |
| 2013/0325103 | A1 | 12/2013 | Arai et al. |
| 2014/0005586 | A1 | 1/2014 | Feinstein |
| 2014/0121761 | A1 | 5/2014 | McDonald et al. |
| 2014/0194970 | A1 | 7/2014 | Chobotov |
| 2014/0200648 | A1 | 7/2014 | Newell et al. |
| 2014/0249617 | A1 | 9/2014 | Argentine et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1 | 4/2015 | Becking et al. |
| 2015/0190221 | A1 | 7/2015 | Schaefer et al. |
| 2015/0257910 | A1 * | 9/2015 | Duong ............... A61F 2/844 623/1.11 |
| 2015/0265444 | A1 | 9/2015 | Kitaoka |
| 2016/0175132 | A1 | 6/2016 | Wilger et al. |
| 2016/0235517 | A1 | 8/2016 | Sethna et al. |
| 2017/0014221 | A1 | 1/2017 | Kelly |
| 2018/0228593 | A1 | 8/2018 | Eaton et al. |
| 2019/0192273 | A1 | 6/2019 | Debus et al. |
| 2019/0223996 | A1 | 7/2019 | McDonald |
| 2020/0038169 | A1 | 2/2020 | Nelis |
| 2020/0038184 | A1 | 2/2020 | McLean |
| 2020/0038211 | A1 | 2/2020 | Kolbel et al. |
| 2020/0214821 | A1 | 7/2020 | Mcdonald |
| 2021/0204954 | A1 | 7/2021 | Nimmo |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0299424 | A1 | 9/2021 | King |
| 2021/0307641 | A1 | 10/2021 | Rumbles et al. |
| 2022/0023080 | A1 | 1/2022 | Mcdonald |
| 2022/0023081 | A1 | 1/2022 | Mcdonald |
| 2022/0273415 | A1 | 9/2022 | Brodie et al. |
| 2022/0378569 | A1 | 12/2022 | Mcdonald |
| 2023/0015592 | A1 | 1/2023 | Debus et al. |

(56) References Cited

U.S. PATENT DOCUMENTS

| | | |
|---|---|---|
| 2023/0119898 A1 | 4/2023 | Kölbel et al. |
| 2023/0225853 A1 | 7/2023 | Zeitani et al. |

FOREIGN PATENT DOCUMENTS

| | | |
|---|---|---|
| EP | 0855171 A2 | 7/1998 |
| EP | 0880979 A1 | 12/1998 |
| EP | 1736116 A2 | 12/2006 |
| EP | 1847236 A2 | 10/2007 |
| EP | 2465471 A2 | 6/2012 |
| EP | 2543342 A1 | 1/2013 |
| EP | 2606852 A1 | 6/2013 |
| EP | 2676639 A1 | 12/2013 |
| EP | 3115022 A1 | 1/2017 |
| EP | 3248572 A1 | 11/2017 |
| EP | 3323385 A1 | 5/2018 |
| GB | 2470083 A | 11/2010 |
| GB | 2491477 A | 12/2012 |
| GB | 2517689 A | 3/2015 |
| JP | H07308330 A | 11/1995 |
| JP | 2013009912 A | 1/2013 |
| JP | 2017042236 A | 3/2017 |
| RU | 2720745 C1 | 5/2020 |
| WO | WO-2003/035130 A1 | 5/2003 |
| WO | WO-2004/017866 A1 | 3/2004 |
| WO | WO-2004/064686 A1 | 8/2004 |
| WO | WO-2006/019626 A2 | 2/2006 |
| WO | WO-2006/034340 A1 | 3/2006 |
| WO | WO-2006/088638 A1 | 8/2006 |
| WO | WO-2008/057569 A1 | 5/2008 |
| WO | WO-2008/088835 A1 | 7/2008 |
| WO | WO-2008/112270 A1 | 9/2008 |
| WO | WO-2009/009376 A2 | 1/2009 |
| WO | WO-2009/082718 A1 | 7/2009 |
| WO | WO-2009/129481 A1 | 10/2009 |
| WO | WO-2009/153768 A1 | 12/2009 |
| WO | WO-2010/053563 A1 | 5/2010 |
| WO | WO-2012/043011 A1 | 4/2012 |
| WO | WO-2012/164292 A1 | 12/2012 |
| WO | WO-2013/152327 A1 | 10/2013 |
| WO | WO-2014/096811 A2 | 6/2014 |
| WO | WO-2014/163957 A1 | 10/2014 |
| WO | WO-2016/054537 A1 | 4/2016 |
| WO | WO-2016/075615 A2 | 5/2016 |
| WO | WO-2016/075615 A3 | 6/2016 |
| WO | WO-2017/136733 A1 | 8/2017 |
| WO | WO-2017/203056 A1 | 11/2017 |
| WO | WO-2018/060716 A1 | 4/2018 |
| WO | WO-2018/156848 A1 | 8/2018 |
| WO | 2018211242 A1 | 11/2018 |
| WO | WO-2020/128417 A1 | 6/2020 |

OTHER PUBLICATIONS

Levack et al., "Rapid Aortic Arch Debranching Using the Gore Hybrid Vascular Graft," Ann Thorac Surg, 95: e163-e165 (2013).

International Search Report and Written Opinion of the International Searching Authority for International Application No. PCT/GB2019/053239 mailed on Jun. 24, 2020.

European Search Report issued in European Patent Application No. 17767890.1, Jul. 28, 2020, 7 pages.

International Preliminary Report on Patentability for Application No. PCT/GB2021/052337 dated Mar. 23, 2023.

International Search Report and Written Opinion for Application No. PCT/GB2018/052742 dated Apr. 9, 2020 (9 pages).

International Search Report and Written Opinion for International Application No. PCT/GB2020/051617 dated Oct. 21, 2020.

International Search Report and Written Opinion issued in PCT Application No. PCT/GB2017/052916, mailed on Feb. 12, 2018.

International Search Report and Written Opinion of the International Searching Authority for International Application No. PCT/GB2017/052602 mailed on Jan. 9, 2018.

International Search Report and Written Opinion of the International Searching Authority for International Application No. PCT/GB2018/051285 mailed on Sep. 11, 2018.

International Search Report and Written Opinion of the International Searching Authority for the International Application No. PCT/GB2018/051127 mailed on Jul. 10, 2018.

Japanese Examination Report for JP Application No. 2019-516423 dated Jul. 27, 2021.

Parodi, J.C., et al., "Transfemoral Intraluminal Graft Implantation for Abdominal Aortic Aneurysms," Annals of Vascular Surgery, vol. 5, pp. 491-499 (1991).

Search and Examination Report for Application No. GB1715658.9 dated Feb. 28, 2018 (8 pages).

Search Report dated Apr. 13, 2018 issued by the Intellectual Property Office of the United Kingdom for Application No. GB1616722.3.

Search Report dated Aug. 8, 2017 issued by the Intellectual Property Office of the United Kingdom for Application No. GB1616722.3.

Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).

United Kingdom Examination Report for GB Application No. 1616722.3 dated Jun. 10, 2021.

United Kingdom Search Report for GB Application No. 1706976.6 dated Jun. 22, 2021.

\* cited by examiner

STENT DEVICE

CROSS REFERENCE TO RELATED APPLICATIONS

This application is a National Stage filing under Section 371 of International Application No. PCT/GB2019/053239, filed on Nov. 15, 2019 and published on Jun. 25, 2020 as WO 2020/128418, and claims priority to Great Britain Patent Application No. 1820898.3, filed on Dec. 20, 2018. The entire disclosures of each of the prior applications are hereby incorporated by reference herein.

FIELD OF THE INVENTION

The present invention relates to a stent device.

BACKGROUND

In this connection, current treatment methods for aortic dissections and aneurysms predominantly utilize conventional surgical grafts and open surgery. Although endovascular treatment methods are also possible, the complexity of maintaining profusion to all major branch vessels radiating from the top of the aortic arch by purely an endovascular approach, means that endovascular treatment methods are currently very limited.

Furthermore, the use of conventional surgical grafts often necessitates a full thoracotomy, namely a major surgical opening of the chest cavity, which typically necessitates a Coronary Artery Bypass and the need to induce hypothermia and cardiac arrest. Undertaking such surgical procedures is not without risk of further complications.

Moreover, known endovascular stent devices and their delivery systems rely on the use of an internal delivery support shaft, typically having an integral moulded tip at its end to facilitate insertion, as well as mounting loops and release wire to support and deploy the stent device. This type of arrangement allows the stent device to be suspended from the delivery system at the tip end. It is held there until unsheathing has been performed, after which it can then be released from the delivery system. After release, which is typically by the removal of a release wire, the supporting internal central shaft and tip assembly must then be fully removed from within the stent device by retracting these items through the inside of the device lumen. These items must be removed carefully to overcome the potential risk of dislodging the previously deployed device by unintentional snagging. To provide this functionality, the delivery system typically necessitates other adjunctive elements such as a guide-wire, which would pass through the internal lumen of the shaft and tip moulding.

Such components prohibit anastomosing the non-stented end of the device to either an adjunctive device or native vessel prior to deployment of the stented section, should that be required.

An object of the present invention is to provide an improved stent device that can alleviate problems associated with what is currently available.

SUMMARY OF THE INVENTION

According to the present invention there is provided a stent device comprising:—a sleeve formed with a plurality of compactable spring ring elements arranged along its length, the sleeve having compacted and expanded states; wherein each said ring element has an undulating profile at the surface of the sleeve so that adjacent ring elements at least partially overlap along the longitudinal extent of the device, the ring elements being compactable against their natural resilience to reduce the outer diameter of the sleeve for allowing housing of the compacted stent device in a frangible sheath, with adjacent ring elements being inter-coupled so as to substantially maintain their axial spacing between the compacted and expanded states.

In this way, the stent device can be compacted so as to adopt a reduced diameter for insertion purposes, the sleeve being in a compressed constrained state when provided within such a frangible sheath. On release from the sheath, the sleeve will, by virtue of the ring elements expand to adopt a larger diameter.

Providing the stent device in a compactable form affords it an integral column stiffness so that internal delivery mechanisms for deploying the stent device can be dispensed with. This simplifies the stent deployment process and importantly bypasses the risks associated with procedures which involve withdrawing such internal delivery mechanisms, in particular dislodgement of the stent device that has just been inserted. The externalised nature of the stent device deployment that is made possible by the stent device of the present invention moreover enhances the ability for anastomosing the stent device to other adjunctive devices or native vessels.

Preferably, the undulating profile of each ring element extends around the surface of the sleeve at the sleeve's periphery. Whilst different undulating ring element profiles may be employed, such as "Z" shapes, each ring element preferably has a hyperbolic paraboloid profile, whereby it is substantially saddle-shaped. In this way, in the compacted configuration, the ring elements can be imbricated, so that they stack axially along the length of the sleeve in an overlapping configuration. The overlapping nature of the ring elements in the compacted configuration enhances the provision of a column stiffness facilitating use with deployment apparatus. In this regard, when in a compacted configuration, the peaks of one ring element overlie the valleys of an adjacent ring element. As such, the close abutment of portions of adjacent ring elements in the compacted configuration affords a column stiffness to the device.

Conveniently, the ring elements are inter-coupled by way of mounting to the sleeve material. Preferably, where adjacent ring elements overlap axially, their circumferential spacing, when in an open configuration of the device, is less than or equal to the maximum change in axial extent of each ring element when moving from an expanded to a compacted configuration. As such, when in the compacted state, fabric between adjacent ring elements is in tension, preventing adjacent rings impinging axially on one another.

Conveniently, the sleeve material is a fabric such as for example gel coated polyester.

Preferably, the ring elements are formed of a nitinol wire. Conveniently, the wire has a diameter in the range 0.08 to 0.24 mm.

The stent device furthermore may have a soft tip at a proximal end. In this respect the soft tip may extend beyond the end of the sheath, when the device is housed in a sheath. The soft tip enhances the functionality of the stent device, affording it atraumatic characteristics allowing it to be deployed without an internal delivery shaft as with known arrangements.

As such, a portion of the proximal end of the stent device is exposed and may be covered in one or more of soft suture or PTFE thread to form an atraumatic tip. In this regard, the soft tip may be formed from stent material at the end of the device. It may comprise a heavy suture on a saddle profile. Further it may comprise one or more additional layers of suture over one or more of the ring elements at the proximal end of the stent device.

DETAILED DESCRIPTION

According to a further aspect of the present invention there is provided a stent device comprising a sleeve formed with a plurality of compactable spring ring elements arranged along its length, wherein a soft end tip is formed at a proximal end of the sleeve, the soft tip end comprising a portion of the sleeve covered in one or more of soft suture material or PTFE thread.

In this regard, the soft tip may be formed from stent material at the end of the device, folded into a ring and held with suture.

The soft tip may comprise a heavy suture on a ring element having a saddle profile. Further, it may comprise one or more additional layers of suture over one or more of the ring elements at the proximal end of the sleeve. With the ring elements having a saddle or hyperbolic paraboloid profile, the soft tip is naturally rounded to optimise its atraumatic characteristics.

FIGURES

Embodiments of the present invention will now be describe by way of example and with reference to the following drawings, of which:—

DETAILED DESCRIPTION OF THE FIGURES

DETAILED DESCRIPTION FOR CARRYING OUT THE INVENTION

Figure 1:
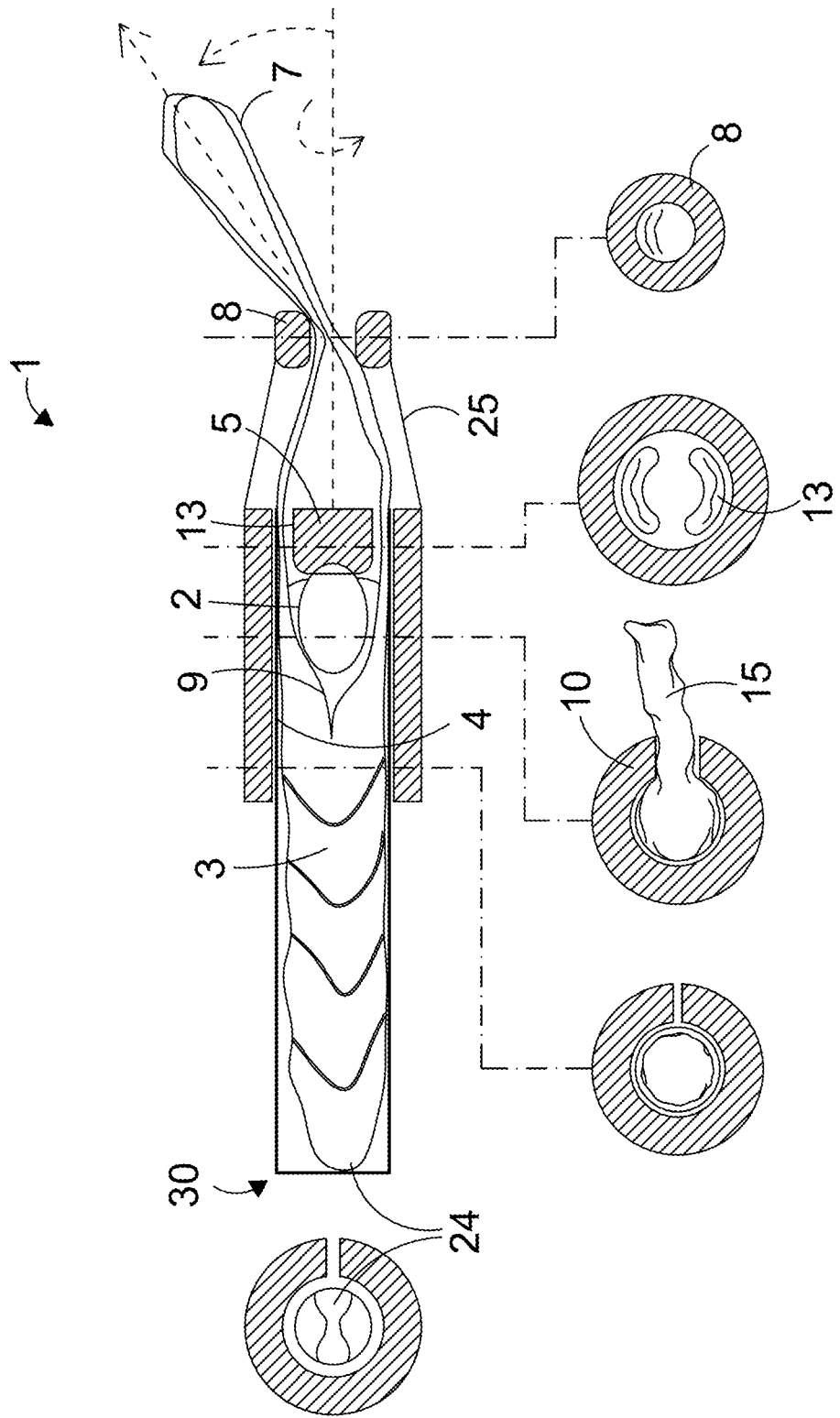
FIG. 1 shows a cross-sectional view of compatible deployment apparatus into which a sheathed stent device of the present invention is located, in accordance with an aspect of the present disclosure.

In this connection, FIG. 1 shows a cross-sectional view of deployment apparatus 1, compatible with a stent device of the present invention, the deployment apparatus having a body 2 into which a sheathed stent device 3 of the present invention is located.

In this regard, the body has a bore 4, dimensioned to allow the sheathed stent device 3 to sit within the bore, but not so tight so as to prevent the sheath material from moving relative to the bore and the stent device.

Figure 2A:
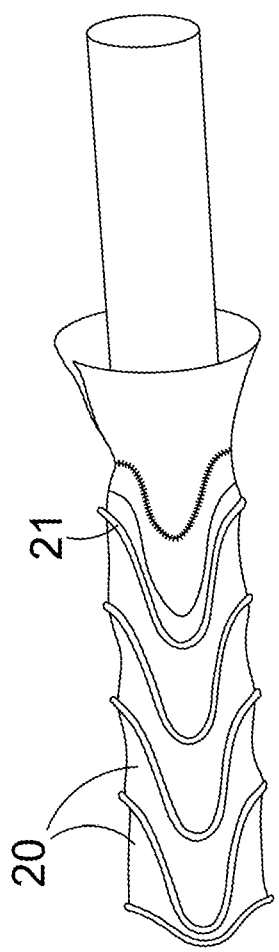
FIGS. 2A and 2B show views of a stent device of the present invention, in accordance with an aspect of the present disclosure.
Figure 2B:
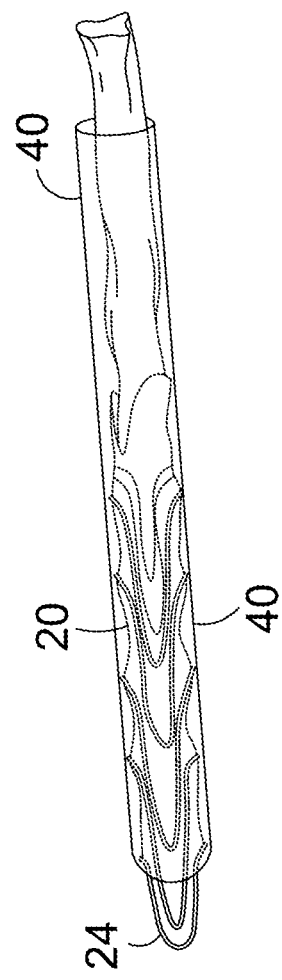

As regards the stent device, as shown unsheathed and sheathed respectively in FIGS. 2*a* and 2*b*, this preferably comprises a lumen or sleeve 20 of fabric, typically gel coated polyester, fitted with a series of spring like "stent elements", typically having ring elements 21 formed from nitinol wire in the shape of an undulating "Z" shaped stent or in the preferred embodiments a saddle ring, namely a hyperbolic paraboloid.

Multiple such ring elements 21 are located along the axis of the lumen and these are attached circumferentially to the fabric by sutured thread, to form the stented device section, which has the capacity to be constrained into a significantly smaller diameter tube, namely sheath 40.

When compacted into the small calibre sheath 40 as shown in FIG. 2*b*, the sheathed stent device (with an appropriate selected oversize) can be readily inserted into the lumen of a branch vessel. Removing the sheath from the stent device enables it to be deployed into the native vessel, where the stented section expands radially outwards. The radially expanding stent elements contact and push onto the internal vessel wall to create a snug fitting non-sutured sealed junction.

The overlapping nature of the ring elements in the compacted configuration affords the sleeve with a column stiffness facilitating use with compatible deployment apparatus, such as shown in FIG. 1.

More specifically, providing the stent device in a radially compactable form affords it an integral column stiffness so that internal delivery mechanisms for deploying the stent device can be dispensed with. This simplifies the stent deployment process and importantly bypasses the risks associated with procedures which involve withdrawing such internal delivery mechanisms, in particular dislodgement of the stent device that has just been inserted.

In this connection, the ring elements are preferably arranged within the sleeve such that the axial spacing of adjacent elements is maintained. In this way, ring element position is maintained across the compaction and deployment states of the stent device.

Figure 3:
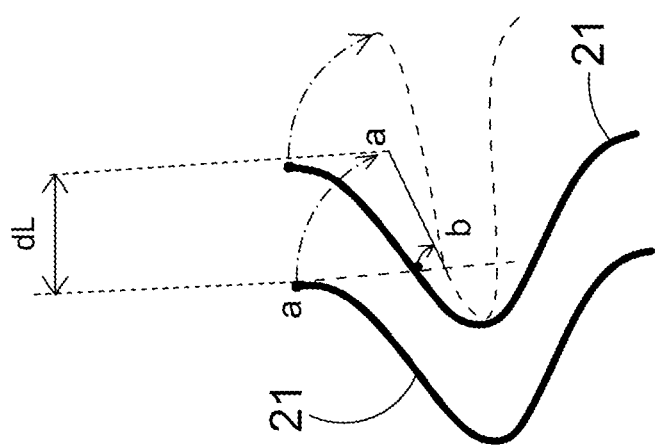
FIG. 3 is a schematic view showing adjacent ring elements of a stent device of the present invention, in accordance with an aspect of the present disclosure.

As shown in FIG. 3, the ring elements 21 are connected to the sleeve material such that where adjacent ring elements overlap axially, their circumferential spacing a-b, when in an open configuration of the device, is less than or equal to the maximum change in axial extent dL of each ring element when moving from an expanded to a compacted configuration. As such, when in the compacted state, fabric between adjacent ring elements is in tension, preventing adjacent rings impinging axially on one another.

In this connection, the device may be configured with a relatively high saddle height, namely a relatively large axial difference between the peaks and the troughs of the ring. Further, the ring inter spacing is preferably less than the saddle height, to provide an overlap of the peaks and valleys of adjacent rings. This property in combination with an adjacent section of supported fabric is utilised to maintain the position of the stent device relative to the body 2, prior to and during the unsheathing process.

As shown in FIG. 1, at or near the distal end of the stented section, there may be provided a section of flexible crimped fabric 15, typically gel coated polyester, which is joined and attached by suturing to form a blood tight continuous endoprothesis lumen. In some embodiments this section may also include a "Y" branch lumen. The non-stented section is provided to enable an endoprothesis to be joined by suturing to either the main prosthesis body or alternatively to a healthy section of native vessel, to reinstate blood profusion to the native branch vessel.

The sheath is preferably thin walled (typically a PTFE material), which has an inherent preposition to tear linearly, without the need for additional grooves or perforations. The sheath may have three sections: a proximal circular section, which has a length slightly longer than the length of the compacted stented section, a tail section at its distal end and a mid-section, where the circular section splits and propagates into the two tail elements.

With the compatible deployment apparatus shown in FIG. 1, these flat ribbon like tail elements 7 originate from the end of the circular section and can be formed by folding. The formed tails are fed through or past a restriction 5 within the body 2 of the compatible deployment apparatus and out into a separate strap element, where they can be tied together to form a singular user interface for sheath removal.

As shown in FIG. 1, the restriction 5 in the bore 2 is configured to obstruct travel of the stent device. The restriction however allows stent device sheath material, namely the tails 7 to pass the restriction for access at the distal end of the body 2.

Whilst any suitable means may be employed to allow passage of the sheath material past the restriction, the compatible deployment apparatus has two arcuate apertures 13 in the face of the restriction 5, the apertures extending longitudinally in the axial direction of the body. The apertures are substantially circumferential and subtend an angle of 90 to 120 degrees. In this connection, the apertures each provide passage for a tail of sheath material 7, the sheath material being split within the bore 4 at point 9.

The body has a side window 10 for allowing the sheathed stent device to be positioned within the body with a crimped section 15 of the stent device exiting the body to the side via the window. The side window hence provides a pathway for the non-stented device fabric 15 to pass through out from the confines of body 2 substantially perpendicularly to the axis of the sheathed sheath within the bore, enabling access to the distal end of the stent device. This end can hence be trimmed in length to suit individual patient anatomy and facilitates suturing to an adjunctive graft or native vessel.

Once the stent device has been sufficiently deployed, it can be removed from the body 2 of the compatible apparatus.

With the above compatible deployment apparatus, the body 2 holds and supports the sheathed stent device 3 to enable the proximal compacted section to be inserted into either a native vessel or an adjunctive stent device body, so that it can be held for subsequent unsheathing and deployment to then enable vessel profusion to be reinstated.

This simplifies the delivery system in terms of its complexity, which together with the reduction in components provides the user with fewer procedural steps and potential risks, enabling a more time efficient and simplified device deployment.

The internal arrangement within the body enables controlled parting of the sheath when the user pulls the strap element. When the sheath is pulled across the internal bore restriction, the circular lumen aspect of the sheath is caused to continue to split, propagating along the two tail elements 7. Simultaneously, the movement applied at the strap is transmitted to the proximal end of the sheath, causing it to slide over the stent device, enabling the compacted stent device to be relieved from its radial constraint. In doing so, the stent device opens and engages the internal lumen of the vessel.

As shown in FIGS. 1, 2A and 2B, the stent may have an integral stent device tip 24 feature. This may be provided at the proximal end of the stented region of the stent device 3, which when compacted within the sheath constraint can protrude beyond the end of the sheath to partially expose said compacted stent device elements covered in soft suture (or PTFE thread) to provide an atraumatic tip like feature.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

The invention claimed is:

1. A stent deployment apparatus comprising:
    a body, the body including:
        a bore defined therein,
        a restriction disposed in the bore,
        at least one aperture extending in a longitudinal direction of the restriction;
        a window disposed within a side of the body;
    a stent device having a proximal end and a distal end defining a stent axis, the stent device disposed within the bore, the stent device including:
        a sleeve formed with a plurality of compactable spring ring elements arranged along its length, the sleeve having compacted and expanded states;
        wherein each said ring element has an undulating profile at a surface of the sleeve so that adjacent ring elements at least partially overlap along a longitudinal extent of the device,
        the ring elements being compactable against their natural resilience to reduce an outer diameter of the sleeve for allowing housing of the compacted stent device in a frangible sheath,
        with adjacent ring elements being inter-coupled so as to substantially maintain their axial spacing between the compacted and expanded states; and a sheath material disposed over at least a portion of the stent device, wherein the restriction is configured to obstruct travel of the stent device but allow passage of the sheath material, with at least a portion of the sheath material passing through the window within the side of the body thereby exiting the body perpendicularly to the stent axis.

2. The stent deployment apparatus as claimed in claim 1, wherein the undulating profile of each ring element extends circumferentially around the surface of the sleeve at the sleeve's periphery.

3. The stent deployment apparatus as claimed in claim 1, wherein each ring element has a hyperbolic paraboloid profile.

4. The stent deployment apparatus as claimed in claim 1, wherein when in a compacted configuration, a plurality of peaks of one ring element overlie a plurality of valleys of an axially adjacent ring element.

5. The stent deployment apparatus as claimed in claim 1, wherein the ring elements are inter-coupled by way of mounting to a material of the sleeve.

6. The stent deployment apparatus as claimed in claim 1, wherein the ring elements are inter-coupled such that where adjacent ring elements overlap axially, a circumferential spacing of the adjacent ring elements, when in an open configuration of the device, is less than or equal to a maximum change in axial extent of each ring element when moving from an expanded to a compacted configuration.

7. The stent deployment apparatus as claimed in claim 1, wherein the ring elements are formed of a nitinol wire with a diameter in the range 0.08 to 0.24 mm.

8. The stent deployment apparatus as claimed in claim 1, wherein the stent device has a soft tip at a proximal end, the soft tip extending beyond an end of the frangible sheath, when the compacted device is housed in the frangible sheath.

9. The stent deployment apparatus as claimed in claim 8, wherein a portion of a proximal end of the device is covered in one or more of soft suture material or PTFE thread.

10. The stent deployment apparatus as claimed in claim 8, wherein the soft tip is formed from multiple suturing at one or more ring elements at a proximal end of the sleeve.

11. The stent deployment apparatus as claimed in claim 1, wherein the ring elements have an arcuate profile.

12. The stent deployment apparatus as claimed in claim 1, wherein the ring elements have a saddle profile.

13. The stent deployment apparatus as claimed in claim 1, further comprising a non-stented section at a distal end.

14. The stent deployment apparatus as claimed in claim 13, wherein the non-stented section includes a flexible crimped fabric.

15. The stent deployment apparatus of claim 1, wherein the at least one aperture has a circumferential shape.

16. The stent deployment apparatus of claim 1, wherein the frangible sheath is configured to be split within the bore.

17. The stent deployment apparatus of claim 16, wherein the at least one aperture defines a passage for a tail of sheath material.

* * * * *